United States Patent [19]
Jenkins

[11] Patent Number: 5,095,622
[45] Date of Patent: Mar. 17, 1992

[54] CLAMPING SCISSOR APPARATUS

[76] Inventor: Herbert L. Jenkins, 11098 Wolfe Rd., Grass Valley, Calif. 95949

[21] Appl. No.: 597,514

[22] Filed: Oct. 15, 1990

[51] Int. Cl.$^5$ .............................. B25F 1/00; B26B 1/00
[52] U.S. Cl. ........................................ 30/134; 30/135
[58] Field of Search ................ 30/232, 236, 233, 231, 30/237, 134, 135; 81/177.3, 415

[56] References Cited

U.S. PATENT DOCUMENTS

| | | | |
|---|---|---|---|
| 2,775,032 | 12/1956 | Sorensen | 30/134 |
| 3,443,313 | 5/1969 | Profy | 30/134 |
| 3,922,781 | 12/1975 | Tippy | 30/134 |
| 4,348,808 | 9/1982 | Nalbandyan | 30/134 |
| 4,404,746 | 9/1983 | Jansson et al. | 30/135 |

Primary Examiner—Douglas D. Watts
Assistant Examiner—Paul M. Heyrana, Sr.
Attorney, Agent, or Firm—Leon Gilden

[57] ABSTRACT

An apparatus is set forth wherein an upper jaw includes a concave recess cooperating with a coaxially aligned planar surface, wherein a bottom jaw provides a cooperating planar clamping surface to cooperate with the upper clamping surface and to effect a severing of a suture and the like secured between the upper and lower jaws.

4 Claims, 4 Drawing Sheets

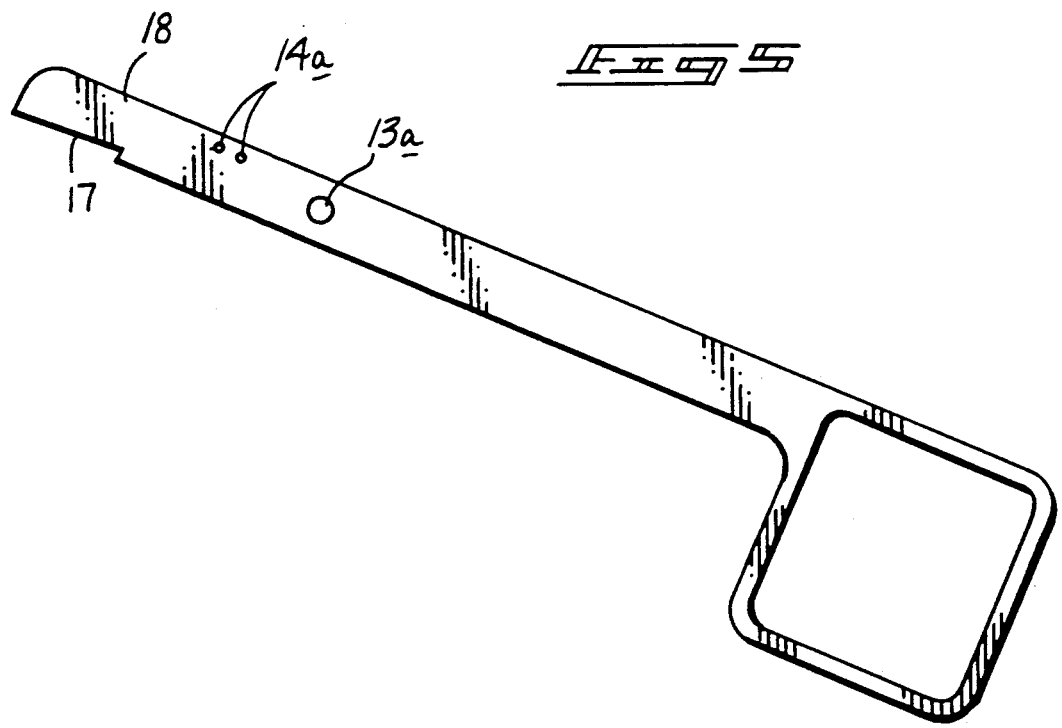
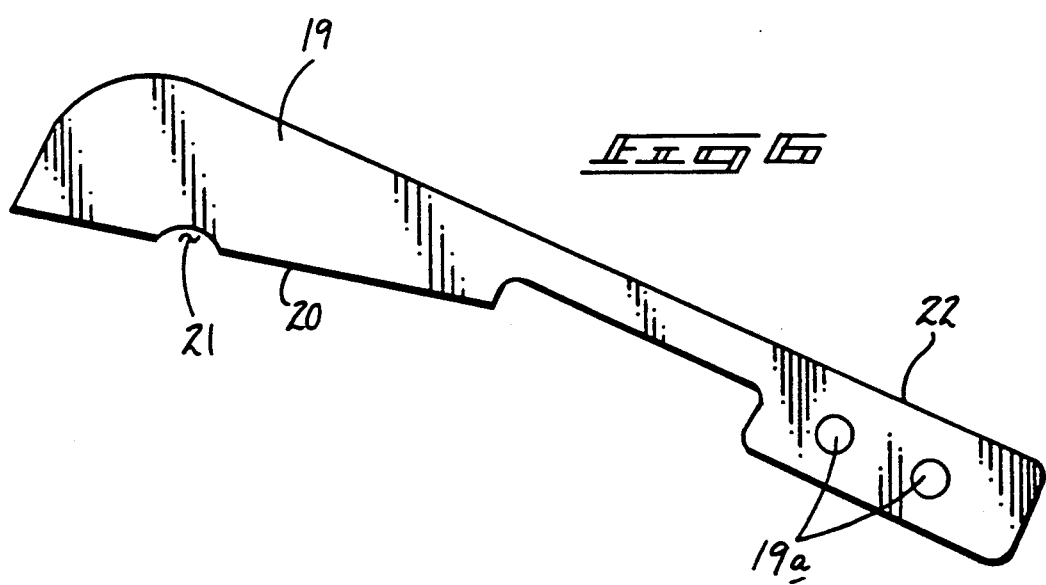

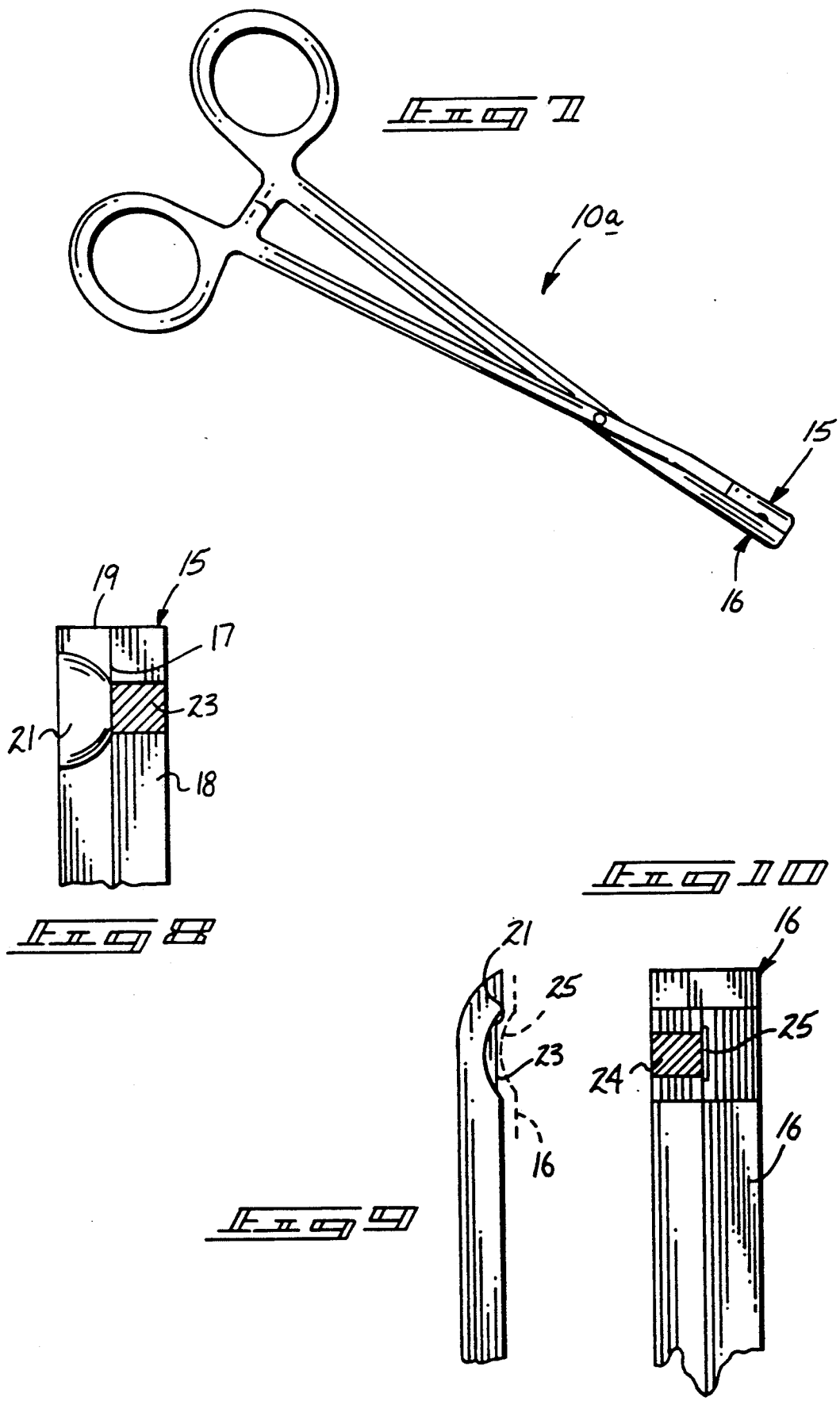

CLAMPING SCISSOR APPARATUS

BACKGROUND OF THE INVENTION

1. Field of the Invention

The field of invention relates to scissor apparatus, and more particularly pertains to a new and improved scissor apparatus wherein the same is arranged for simultaneous clamping and severing of sutures and the like.

2. Description of the Prior Art

Various scissor structure has been provided in the prior art to effect severing of various components. A suture clamping and severing scissor is set forth in U.S. Pat. No. 4,246,609 to Lasner wherein an elongate clamping member is positioned on one of a plurality of pivoted jaws of a scissor structure to enhance clamping during severing of a suture member.

U.S. Pat. No. 3,553,819 to Johnson, et al. sets forth a scissor-like tool structure arranged for severing utilizing opposed hollow ground jaws.

U.S. Pat. No. 4,140,124 to Cirrhotic sets forth a handle structure providing abutment portions for enhanced grasping thereof during a severing procedure.

U.S. Pat. No. 3,834,021 to White, et al. sets forth a cutting instrument utilizing cooperating jaws for severing pivotal relative to one another utilizing sleeve structure relatively mounted in a sliding relationship to effect severing of an object therebetween.

U.S. Pat. No. 3,771,207 to Compile sets forth a structure for the severing of various cable-like portions that are directed through aligned openings within the jaw structure of the organization.

As such, it may be appreciated that there continues to be a need for a new and improved clamping scissor apparatus as set forth by the instant invention which addresses both the problems of ease of use as well as effectiveness in construction and in this respect, the present invention substantially fulfills this need.

SUMMARY OF THE INVENTION

In view of the foregoing disadvantages inherent in the known types of scissor apparatus now present in the prior art, the present invention provides a clamping scissor apparatus wherein the same utilizes cooperating jaws, wherein the jaws include cooperating clamping and severing structure to effect simultaneous clamping and severing of a suture directed therebetween. As such, the general purpose of the present invention, which will be described subsequently in greater detail, is to provide a new and improved clamping scissor apparatus which has all the advantages of the prior art scissor apparatus and none of the disadvantages.

To attain this, the present invention provides an apparatus wherein an upper jaw includes a concave recess cooperating with a coaxially aligned planar surface, wherein a bottom jaw provides a cooperating planar clamping surface to cooperate with the upper clamping surface and to effect a severing of a suture and the like secured between the upper and lower jaws.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved clamping scissor apparatus which has all the advantages of the prior art scissor apparatus and none of the disadvantages.

It is another object of the present invention to provide a new and improved clamping scissor apparatus which may be easily and efficiently manufactured and marketed.

It is a further object of the present invention to provide a new and improved clamping scissor apparatus which is of a durable and reliable construction.

An even further object of the present invention is to provide a new and improved clamping scissor apparatus which is susceptible of a low cost of manufacture with regard to both materials and labor, and which accordingly is then susceptible of low prices of sale to the consuming public, thereby making such clamping scissor apparatus economically available to the buying public.

Still yet another object of the present invention is to provide a new and improved clamping scissor apparatus which provides in the apparatuses and methods of the prior art some of the advantages thereof, while simultaneously overcoming some of the disadvantages normally associated therewith.

Still another object of the present invention is to provide a new and improved clamping scissor apparatus wherein the same provides cooperating pivoted jaws, wherein the pivoted jaws effect a simultaneous clamping and severing of a suture directed therebetween.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 5 is an orthographic view, taken in elevation, of the first handle portion.

FIG. 6 is an orthographic side view, taken in elevation, of the first handle jaw guide plate.

FIG. 7 is an orthographic side view, taken in elevation, of the further example of the instant invention.

FIG. 8 is an orthographic plan view of the top jaw structure of the invention as depicted in FIG. 7.

FIG. 9 is an orthographic side view of the top jaw FIG. 7.

FIG. 10 is an orthographic plan view of the bottom jaw structure of FIG. 7.

DESCRIPTION OF THE PREFERRED EMBODIMENT

Figure 1:
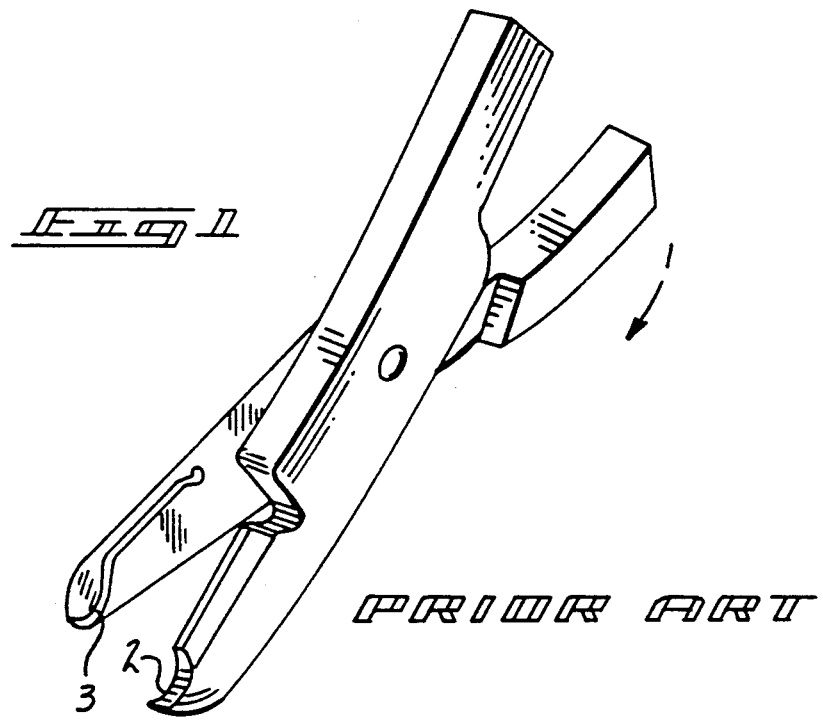
FIG. 1 is an isometric illustration of a prior art scissor apparatus.

With reference now to the drawings, and in particular to FIGS. 1 to 10 thereof, a new and improved clamping scissor apparatus embodying the principles and concepts of the present invention and generally designated by the reference numeral 10 will be described.

Figure 2:
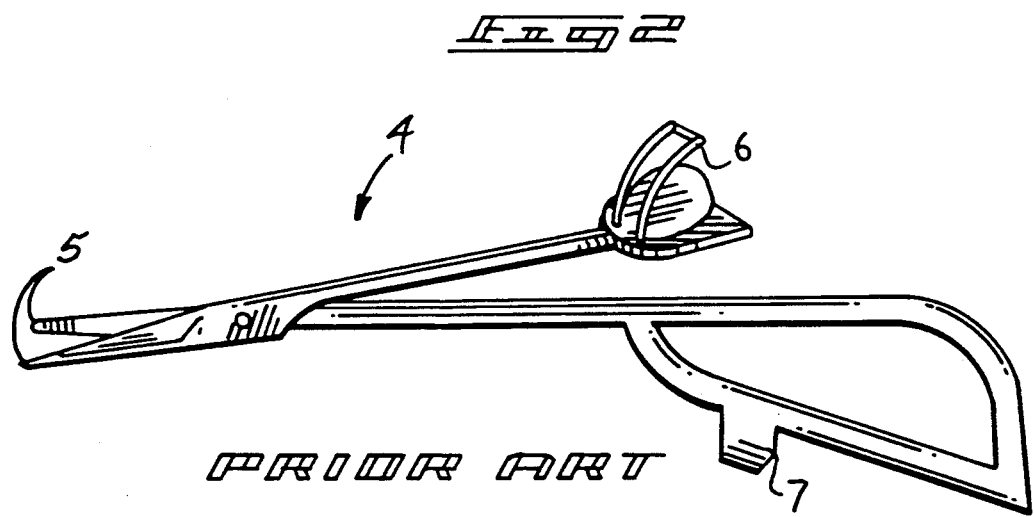
FIG. 2 is an isometric illustration of a further prior art scissor apparatus.
Figure 3:
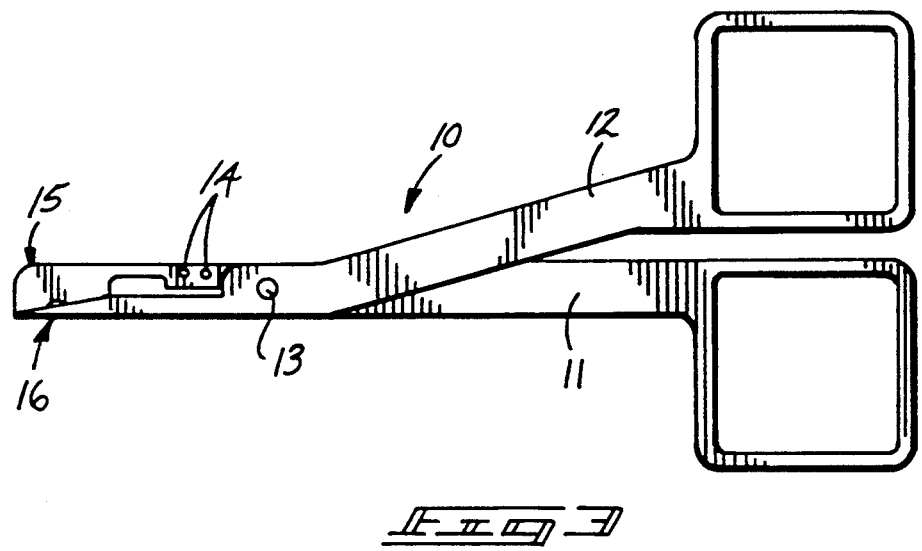
FIG. 3 is an orthographic side view, taken in elevation, of the instant invention.

FIG. 1 illustrates a prior art scissor apparatus 1, wherein a first jaw 3 covers a second jaw 2 to effect severing of a suture member, with a resilient member mounted to the jaw 3 to enhance clamping of the suture during severing, in a manner as set forth in U.S. Pat. No. 4,246,698. FIG. 2 illustrates a prior art scissor apparatus 4, wherein spaced jaws 5 cooperate with scissor-like handles, wherein a first handle portion 6 receives a thumb member, and wherein an abutment member 7 mounted to the second handle portion provides abutment for a hand of an individual, in a manner as set forth in U.S. Pat. No. 4,140,124.

Figure 4:
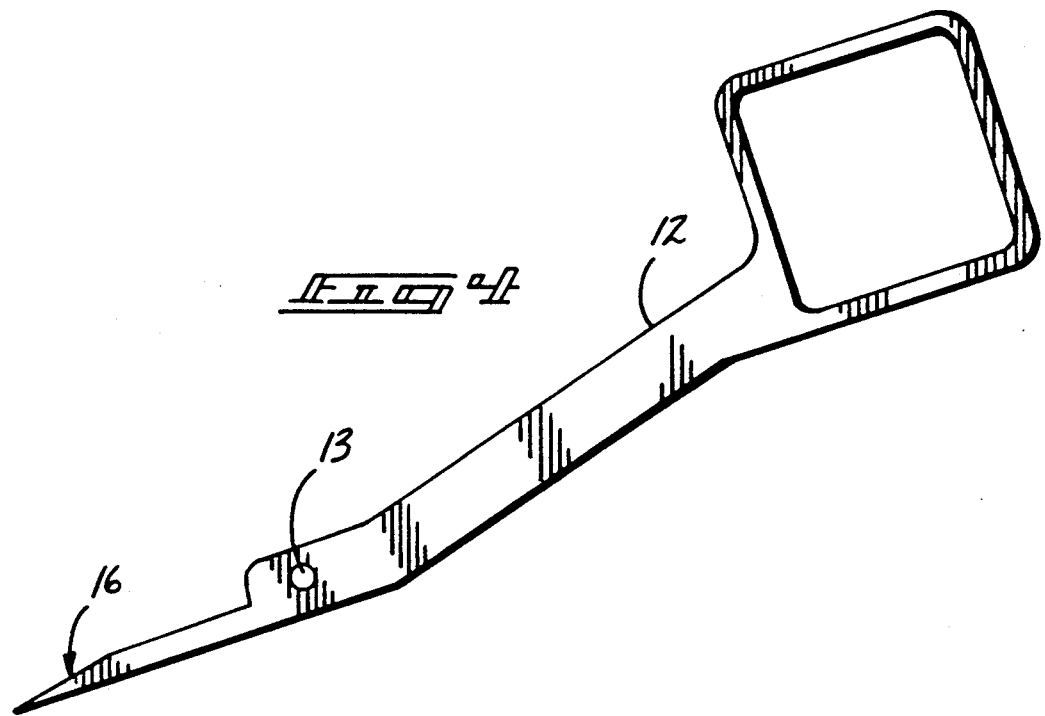
FIG. 4 is an orthographic side view, taken in elevation, of the handle portion.

More specifically, the clamping scissor apparatus 10 of the instant invention essentially comprises a first handle 11 pivotally mounted to a second handle 12 about a pivot axle 13. The first handle 11 includes a first jaw 18, including a first jaw support shank edge 17 cooperative with a first jaw guide plate 19 mounted thereon, wherein the guide plate includes a guide plate support opening 19a to secure the guide plate to threaded fastener bores by mounting fasteners 14 through the support openings 19a of the first jaw guide plate 19 as illustrated in FIGS. 8 and 10, the first grasping surface of a predetermined length, less than a semi-spherical diameter defined by the recess 21, cooperates with the second grasping surface 24, also of an equal predetermined length. The first handle 11 thereby defines the first jaw member 15, with the second handle 12 utilizing a second cooperating jaw member 16, as illustrated in FIG 4. FIG. 10a is illustrative of a modified scissor apparatus 10a, wherein the organization is arranged for use by a left hand individual. The first jaw member 15 includes a semi-spherical recess guide 21 coaxially oriented with a roughened first grasping surface 23 within the same first jaw 18. The first grasping surface 23 cooperates with a roughened second grasping surface 24 mounted on the cooperating second jaw member 16. If required, a semicircular severing blade 25 is mounted at the intersection defined between the roughened second grasping surface 24 and arranged to cooperate with the first jaw support shank edge 17 to effect severing of a suture directed therethrough. The semi-spherical guide recess 21 in use guides the suture in the downward directing of the first jaw member 15 over the suture to effect convenience of severing of the suture. If required, the guide plate mounting rail 22, including the guide plate support openings 19a, permits ease of replacement of the first jaw guide plate 19 to utilize various guide recesses 21 in cooperation with the cooperating first and second grasping surfaces 23 and 24.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A clamping scissor apparatus comprising, in combination, a first handle pivotally mounted to a second handle, the first handle including a first jaw mounted at a forward terminal end of the first handle, and the second handle including a second jaw mounted at a forward terminal end of the second handle cooperating with the first handle, and the first jaw including a first grasping surface, the second jaw including a second grasping surface, the first and second grasping surfaces arranged to secure a workbox to be directed therethrough, and a severing blade mounted in planar alignment, with an exterior face of the first jaw to effect severing of the severing blade in cooperation with the second jaw, and wherein the first jaw includes a first jaw guide plate, the first jaw guide plate including an elongate mounting rail, the elongate mounting rail including a plurality of apertures directed therethrough, the plurality of apertures coaxially aligned with a plurality of mounting bores directed through the first jaw, and a plurality of fasteners directed through the first apertures and the first bores to secure the guide plate to the first jaw, the guide plate including a semi-spherical recess, the semi-spherical recess coaxially aligned with the first grasping surface.

2. An apparatus as set forth in claim 1 wherein the semi-spherical recess is defined by a semi-spherical recess diameter and the first grasping surface is defined by a predetermined length, wherein the semi-spherical recess diameter is greater than the predetermined length.

3. An apparatus as set forth in claim 2 wherein the second grasping surface is defined by a length equal to the predetermined length.

4. An apparatus as set forth in claim 3 wherein the second grasping surface is arranged and extends medially of the second jaw, and the severing blade mounted medially of the second jaw to cooperate with an inner face between the first jaw guide plate and the first grasping surface.

* * * * *